United States Patent [19]

Leeper et al.

[11] 4,419,096

[45] Dec. 6, 1983

[54] ELASTOMERIC BLADDER ASSEMBLY

[75] Inventors: Harold M. Leeper, Mountain View; Nikki Baumrind; John R. Peery, both of Palo Alto, all of Calif.

[73] Assignee: ALZA Corporation, Palo Alto, Calif.

[21] Appl. No.: 350,585

[22] Filed: Feb. 22, 1982

[51] Int. Cl.³ .............................................. A61M 5/00
[52] U.S. Cl. ........................... 604/132; 128/DIG. 12; 222/107; 222/215; 222/386.5
[58] Field of Search ............. 128/DIG. 12; 604/890, 604/891, 18, 48, 49, 93, 131, 132, 183, 403, 415; 222/95, 105, 106, 206, 212, 386.5, 215, 107

[56] References Cited

U.S. PATENT DOCUMENTS

| | | | |
|---|---|---|---|
| 3,361,303 | 1/1968 | Jacuzzi | 128/DIG. 12 |
| 3,895,631 | 7/1975 | Buckles et al. | 604/132 |
| 3,993,069 | 11/1976 | Buckles et al. | 604/132 |
| 4,140,117 | 2/1979 | Buckles et al. | 604/132 |
| 4,201,207 | 5/1980 | Buckles et al. | 604/132 |
| 4,299,222 | 11/1981 | Eckenhoff | 604/93 |
| 4,318,400 | 3/1982 | Peery et al. | 604/18 |

*Primary Examiner*—C. Fred Rosenbaum
*Assistant Examiner*—Michelle N. Lester
*Attorney, Agent, or Firm*—Steven F. Stone; Edward L. Mandell; Paul L. Sabatine

[57] ABSTRACT

Elastomeric bladder assemblies designed for operation at constant pressure to maintain a constant dispensing rate for the contents exhibit a pressure spike shortly before the end of the duty cycle. This pressure spike may be prevented by including within the lumen of the bladder a bolus forming means which prevents the bladder from collapsing to a cylindrical configuration.

9 Claims, 4 Drawing Figures

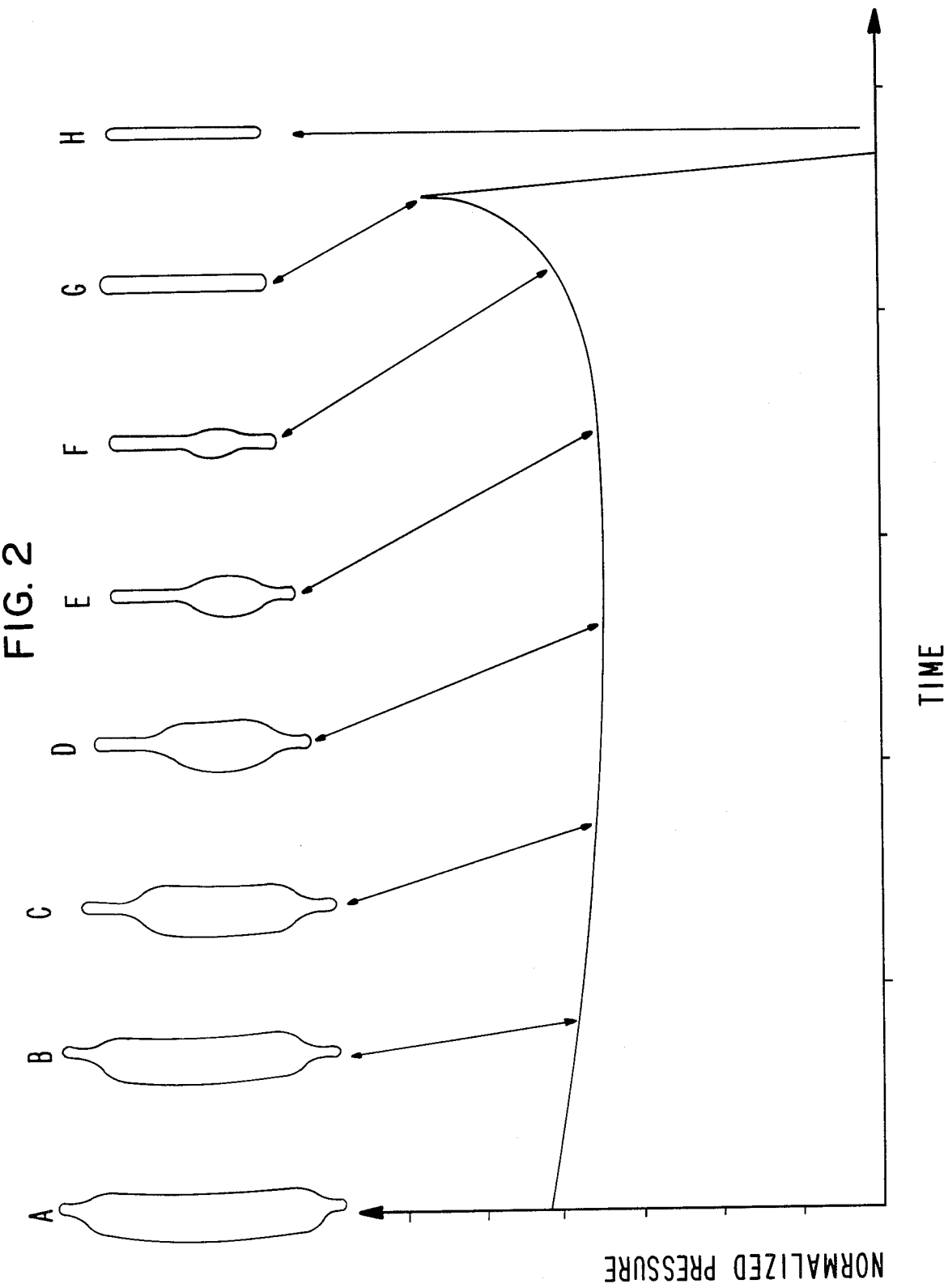

ELASTOMERIC BLADDER ASSEMBLY

TECHNICAL FIELD

This invention relates to an elastomeric bladder assembly which is intended to dispense its contents at a substantially constant rate over a substantial period of time.

BACKGROUND OF THE INVENTION

This invention is an improvement in the elastomeric bladder assemblies disclosed in co-pending, co-assigned patent application Ser. No. 312,430 filed Oct. 19, 1981 which is a continuation of Ser. No. 113,224 filed Jan. 18, 1980 for Medical Infuser by J. R. Peery, P. F. Carpenter and W. K. Griesinger and in U.S. Pat. No. 4,201,207 which in turn were improvements over the devices disclosed in U.S. Pat. Nos. 3,895,631 and 4,140,117 all patents being commonly owned. These devices all employed elastomeric collapsing bladders in medical infusers which were adapted to administer a pre-determined amount of pharmaceutically active material to a subject over a prolonged period of time. Since the flow rate of the pharmaceutical agent from these devices is dependent upon the pressure generated within the elastomeric bladder, it is important the pressure generated by the elastomeric bladder remain relatively constant throughout a substantial portion of the operating lifetime of the device. The above-described devices are generally satisfactory for their intended purposes and all represent significant advances over the art. Nevertheless, it has been observed that in the terminal portion of the dispensing cycle, a pressure increase or "spike" occurs just prior to the emptying of the contents of the bladder which causes an increase in the flow rate from the device immediately prior to the final tail off the fluid flow at the end of the duty cycle. While this increase in flow rate is acceptable in most applications, it could present a problem in those particular instances in which an extremely potent drug is being administered. Presently, the only way this increase in flow rate can be eliminated is to remove or change the bladder prior to complete emptying, with a concommitant loss of unused drug.

According to this invention, however, I have provided a means whereby the terminal pressure spike may be eliminated while still permitting total utilization of the drug within the bladder. Accordingly, it is an object of this invention to provide an elastomeric bladder assembly whch exerts a substantially constant pressure on its contents throughout its duty cycle. It is another object of this invention to provide means within a collapsing elastomeric bladder for maintaining the pressure generated within the bladder at a substantially constant rate throughout is entire collapse. These and other objects of the invention will be readily apparent from the following description of the invention with reference to the accompanying drawings wherein:

FIG. 2 is a pressure time trace produced by the device of FIG. 1, illustrating the configuration of the collapsing elastomeric bladder at various stages of operation;

Figure 1:
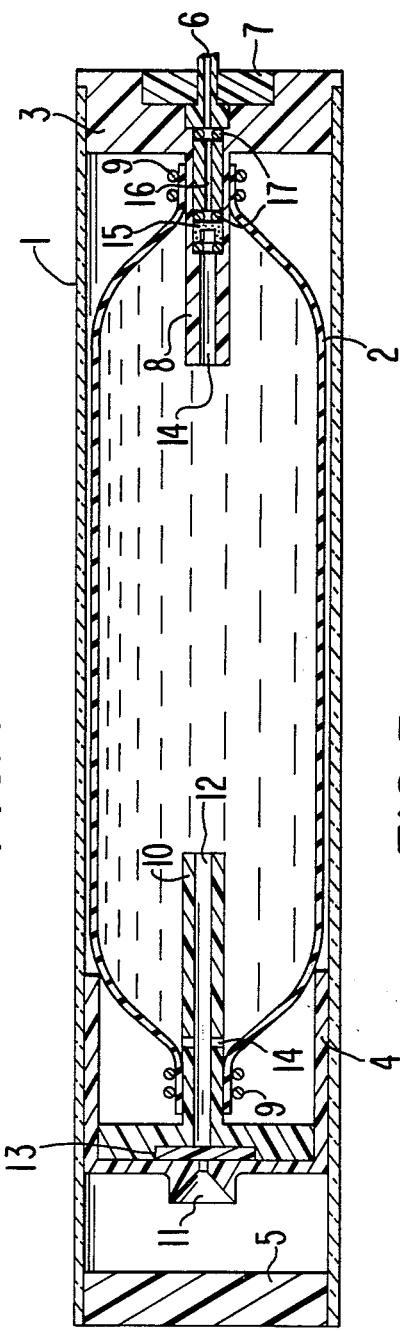
FIG. 1 is a cross-section view through a preferred embodiment of the devices of the prior art.

Referring now to FIG. 1, the structure of the prior art device disclosed in U.S. patent application Ser. No. 113,224 noted above, is shown. This device consists of a tubular housing 1 containing an elastomeric bladder 2. The bladder 2 is connected at its discharge end to plug/flow control assembly 3 mounted in one end of the housing 1 and at its other end to piston/filling assembly 4 which is slidably received within housing 1. The end of housing 1 may be sealed with plug 5 which may be provided with means, not shown, for venting the space between the plug 5 and assembly 4 to the atmosphere. A delivery conduit 6 is mounted in plug/flow control assembly 3 by means of plug 7 and is adapted to deliver the contents of the bladder to a subject by a standard infusion needle or other conventional apparatus. Bladder 2 is mounted to assembly 3 by any suitable means such as spring clip 9 engaging hollow post 8 extending from the interior surface of assembly 3. The other end of bladder 2 is similarly affixed to a hollow post 10 extending from the interior surface of assembly 4. Assembly 4 is provided with a filling port 11 which communicates with the interior of bladder 2 through the port 12 in post 10 through a puncturable, resealable septum 13 made from rubber or other suitable materials known to the art. Septum 13 is adapted to by punctured by a filling needle and to be capable of resisting, without leaking or rupturing, the pressure generated within the inflated bladder. Transverse ports 14 may also be provided in post 10 to facilitate filling. Post 8 is similarly provided with a central port 14 and contains a filter element 15 and a capillary flow control element 16 which in combination with the predetermined pressure produced by bladder 2 provides for a constant delivery rate of fluid from the bladder to delivery conduit 6. O-ring seals 17 are provided as necessary at the transition points between the various elements within the assembly 3. FIG. 1 shows the device in its fully filled condition ready for dispensing of fluid. It should be understood that in the uninflated condition, assembly 4 will have slid into housing 1 until the opposing ends of posts 10 and 8 are in abutment with their internal ports 12 and 14 in alignment and bladder 2 will be collapsed around the posts 10 and 8. In the deflated condition, posts 10 and 8 act as a core substantially filling the lumen of the empty bladder 2. This permits the substantially complete expulsion of the contents of the bladder while also acting as a shield for the bladder against puncture when the filling needle is introduced through septum 13.

Referring now to FIG. 2, a pressure-time trace of a device of FIG. 1 is shown together with the observed configuration of the bladder at various points in its operating cycle. As can be seen, the pressure within the bladder remains substantially constant, (within approximately ±10% of mean operation pressure) until shortly before the end of the duty cycle at which point a relatively rapid increase in pressure outside the desired operating range is observed.

As can be seen from FIG. 2, as the contents of the bladder are expelled, the shape of the aneurism in bladder 2 changes from a roughly sausage shaped configuration at the beginning of the duty cycle (A and B) to an aneurism having bulbar and cylindrical portions (C, D E and F) to a substantially cylindrical aneurism (G and H). As is also seen from FIG. 2, the pressure spike occurs at the point at which the configuration of the aneurism changes from partially bulbar and partially cylindrical to substantially cylindrical (between F and G).

According to this invention, the pressure spike is eliminated by the inclusion within bladder 2 of means to maintain the aneurism in its slightly bulbar configuration.

Figure 3:
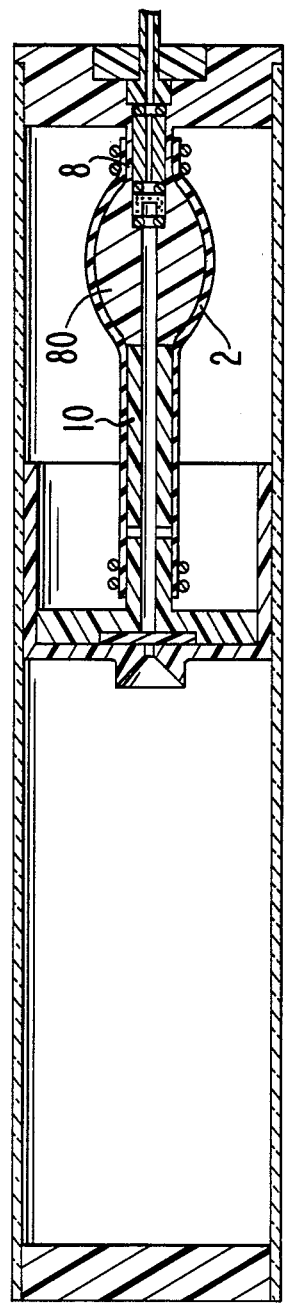
FIG. 3 is a view of a preferred embodiment of this invention.

Referring now to FIG. 3, a preferred embodiment of this invention is shown with common elements corresponding to those shown in FIG. 1. In FIG. 3, the device is shown in its fully deflated condition as it would appear both prior to the time that it is filled with fluid and at the end of its duty cycle after it has expelled its contents. Lumen filling core means 10 and 8 have been configured such that the internal configuration of collapsed bladder 2 mimics the internal configuration of a bladder at the point just prior to the disappearance of the bulbar aneurism. The preferred configuration of the core means for any particular bladder can therefore be readily determined by visual observation of the performance of the bladder during its duty cycle such as is shown in FIG. 2. In general, however, it is preferred that the external diameter of the cylindrical portion 10 of the lumen filling core means be slightly larger than the internal diameter of the bladder in its fully collapsed, relaxed condition, and the bulbar, portion 80 of lumen filling core means 8 should be sufficient to provide a clearly observable bulb having an diameter greater than that of the cylindrical portion. It should be noted that although the location of the bulbar aneurism in the prior art device is somewhat random occurence the provision of the bulbar portion 80 on the core means predetermines the location of the bulbar aneurism.

Although the preferred embodiment employs core means which fill the entire lumen of the deflated bladder to obtain the desired end configuration for the interior of the bladder, this invention can also be utilized in bladder assemblies which do not have the entire lumen of the bladder filled with a core at the end of the duty cycle. Thus in the bladders which are shown, for example, in U.S. Pat. No. 3,895,631, a bulbar post with a fluid passage through the interior could be mounted in one end of the bladder assembly. This would result in the cylindrical portion of the aneurism being left with a residue of usable drug and would result in the elimination of the other advantages associated with the lumen filling core means. In the case where just a bolus forming means 80 is included within the bladder, its diameter should be sufficiently greater than the internal diameter of the fully collapsed bladder to produce a pronounced bolus in the bladder while the cylindrical portion is still capable of undergoing radial contraction.

Figure 4:
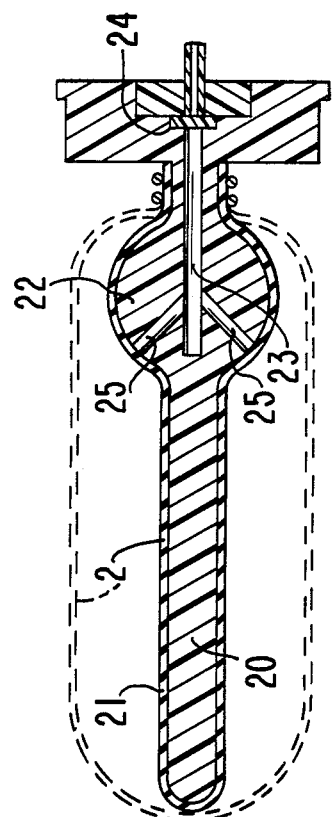
FIG. 4 is a view of another embodiment of this invention.

Referring now to FIG. 4, another embodiment of the invention is shown. In FIG. 4, unitary core 20 having a generally cylindrical portion 21 and bulbar bolus portion 22 is inserted within elastomeric bladder 2. Core 20 is provided with a port 23 sized to receive a needle or other tube for introduction and withdrawal of fluid into and out of the device through resealable septum 24 and ports 25 extending through the wall of bolus 22. In this embodiment, core 20 has an axial length substantially equal to the axial length of bladder 2 in its inflated condition (shown in dotted lines). In this embodiment as a result of the prestressing of the bladder to its inflated length by core 20, inflation and contraction occurs only in the radial direction. Since there is no axial component of contraction, design for constant pressure is simplified.

EXAMPLE

A preferred embodiment of this invention is constructed according to FIG. 3, using a 7.2 cm long polyisoprene rubber bladder having a wall thickness of 1.00 mm and an internal diameter of 4.30 mm in the unstressed condition. The external diameter of the cylindrical portion of the lumen filling means is 6.15 mm and the bulb is spherical having an external diameter of 10.5 mm. In operation this bladder generates a pressure of 455 mm±10% and without a terminal pressure spike.

While this invention has been described with respect to specific embodiments thereof, it should not be construed as being limited thereto. Various modifications may be made by workers skilled in the art without departing from the scope of this invention which is limited only by the following claims.

We claim:

1. A positive expulsion bladder assembly comprising, in combination, an elastomeric bladder having a central lumen with a predetermined, unexpanded, internal diameter and lumen filling core means within said bladder, said core means being provided with a bulbar portion having a diameter greater than said predetermined internal diameter.

2. The assembly of claim 1 wherein said lumen filling core means comprises a cylindrical portion adjacent to said bulbar portion, the external diameter of said cylindrical portion being less than the diameter of the bulbar portion and larger than said predetermined internal diameter of said bladder.

3. The apparatus of claim 2 wherein the combined length of said bulbar and cylindrical portions is substantially equal to the inflated length of said bladder.

4. The apparatus of claim 2 wherein the combined length of said bulbar and cylindrical portion is less than the inflated length of said bladder.

5. The apparatus of claim 1, 2, 3 or 4 further comprising fluid communicating means extending through said core means providing communication between the interior of said bladder and the exterior of the device.

6. In a positive expulsion device, comprising an elastomeric bladder having a predetermined, unexpanded internal diameter defining a central lumen, means for charging a fluid into the lumen of said bladder and for withdrawing fluid from said bladder, whereby said bladder may be inflated with said fluid and said fluid thereafter discharged under the influence of the pressure generated by the expansion of said bladder, and lumen filling means within said bladder in its unexpanded condition; the improvement whereby peaks in the pressure generated by said bladder on its fluid contents may be reduced, which comprises a bulbar portion on said lumen filling means which bulbar portion has a diameter greater than said predetermined internal diameter.

7. A positive expulsion device according to claim 6, wherein said lumen filling means comprises a cylindrical portion adjacent to said bulbar portion, the external diameter of which is smaller than the diameter of the bulbar portion and larger than the predetermined unexpanded internal diameter of said bladder.

8. The apparatus of claim 6, wherein the combined length of said bulbar and cylindrical portions are substantially equal to the inflated length of said bladder.

9. The apparatus of claim 6, wherein the combined length of said bulbar and cylindrical portions is less than the inflated length of said bladder.

* * * * *